June 10, 1975 W. A. WARRINER Plant Pat. 3,727
ROSE PLANT
Filed March 21, 1974
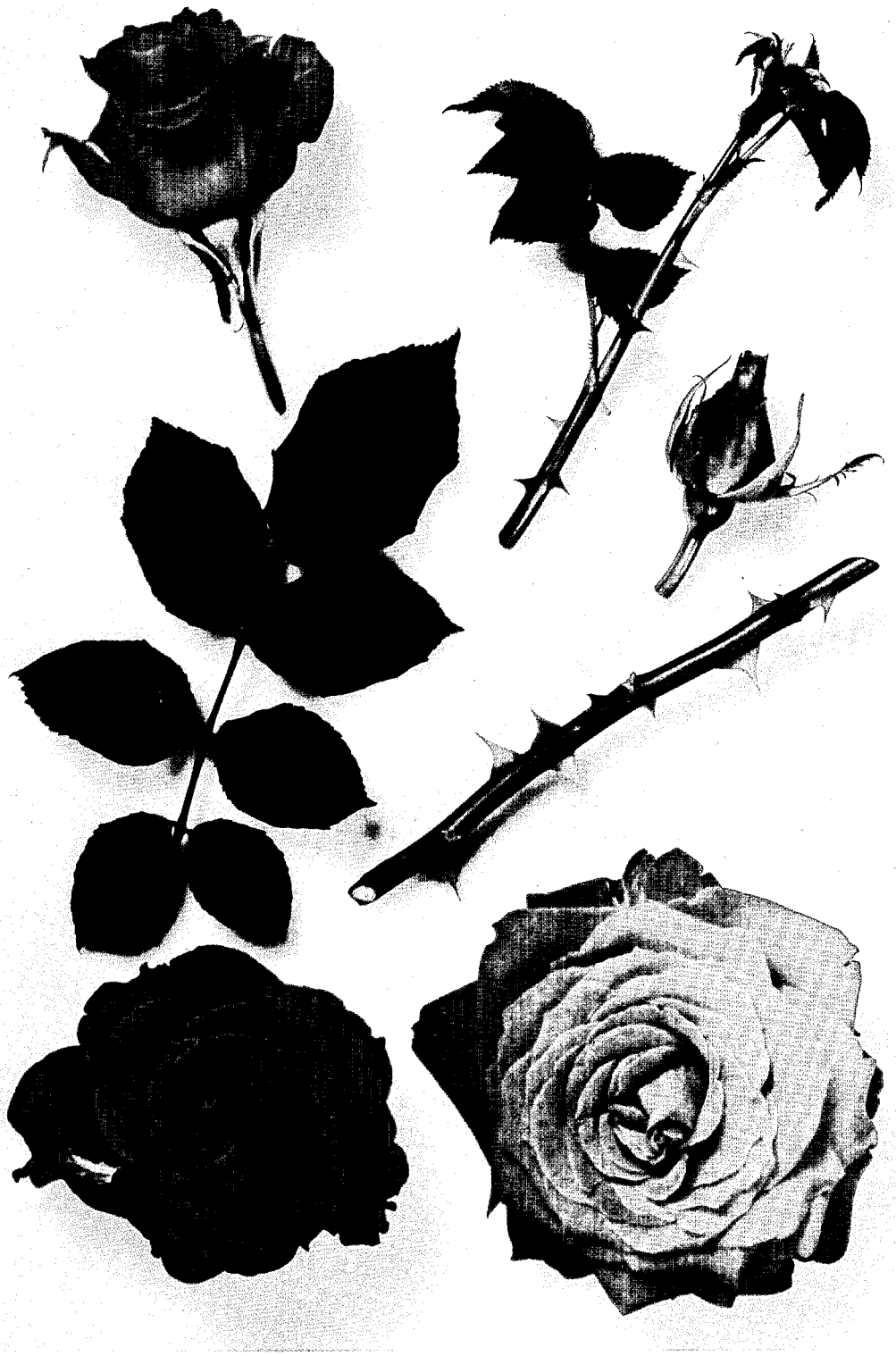

United States Patent

Plant Pat. 3,727

Patented June 10, 1975

3,727

ROSE PLANT

William A. Warriner, Tustin, Calif., assignor to Jackson & Perkins Company, Medford, Oreg.

Filed Mar. 21, 1974, Ser. No. 453,302

Int. Cl. A01h 5/00

U.S. Cl. Plt.—20 1 Claim

The present invention relates to a new and distinct cultivar of rose plant of the hybrid tea class which was originated by me by crossing the cultivar Bridal Pink, U.S. Plant Pat. 2,851, with pollen from an unnamed cultivar used only for breeding.

The primary objective of this breeding was to produce a new rose cultivar of vigorous growth, high production of cut flowers, of bright "non-bluing" red color, long vase life. This objective was substantially achieved along with other desirable improvements over older cultivars, as evidenced by the following unique combination of characteristics which are outstanding in the new cultivar and which distinguish it from its parents as well as from all other cultivars of which I am aware:

1. A very vigorous, upright, not angular habit of growth.
2. Strong, straight stems.
3. A tendency, especially during rapid periods of growth to produce several side buds immediately below the terminal flower.
4. Foliage that is of medium size, undulated edges like its parent, Bridal Pink.
5. Foliage color is a darker, bluer green than other similar red hybrid tea cultivars such as Tonight, Forever Yours and Red American Beauty.
6. Buds and open flowers are generally smaller than Forever Yours and Red American Beauty and rate of opening is slower.
7. Little or no fragrance.

Asexual reproduction of this new variety by budding, as performed at Wasco, Calif., proves that the foregoing characteristics and distinctions reproduce truly and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose variety with color terminology in accordance with Munsell Book of Color and/or Wilson's Horticultural Color Chart, except where ordinary dictionary significance of color is indicated.

Parentage: Seedling.
- *Seed parent.*—Bridal Pink, U.S. Pl. Pat.
- *Pollen parent.*—Unnamed cultivar.

Classification:
- *Botanic.*—Rosa hybrid.
- *Commercial.*—Hybrid tea.

FLOWER

Observations were made in mid-September in Irvine, Calif., from plants in a greenhouse.

Blooming habit: Continuous.

Bud:
- *Size.*—One and one-fourth to one and one-half inches when petals start to unfurl.
- *Form.*—Pointed, broad base.
- *Color.*—When sepals first divide. Red 5.0 R 3/12 Munsell. When half blown; upper side of petals 4.5 R 4/14 (Munsell); lower side of petals—3.0 R 4/12 (Munsell).
- *Sepals.*—Color: Outer surface—green 7.5 GY 6/6 (Munsell); inner surface 7.5 GY 4/6 (Munsell) covered with fine tomentum. Three appendaged sepals lightly appendaged, slightly hairy edged.
- *Receptacle.*—Color: Near 7.5 GY 4/6 (Munsell). Shape: Funnel. Size: Large. Surface: Smooth.
- *Peduncle.*—Length: Long. Surface: Smooth. Color: Light green, near 7.5 GY 4/6 (Munsell). Strength: Stiff, erect, heavy.
- *Opening.*—Very slowly—outer petals tend to fall away before center petals fold out.

Bloom:
- *Size.*—Large. Average size when fully expanded, four inches.
- *Borne.*—Singly and several together.
- *Stems.*—Long, strong.
- *Form.*—When first open—high center. Performance—outer petal edges slightly curled. Very little quilling (or pointing) of petals.
- *Petalage.*—Number of petals under normal conditions 45–50.
- *Color.*—Center of flower: Upper side of petals—Near 4.0 R 3-5/14 (Munsell) or Currant Red 821/ (Wilson). Reverse side of petals—Rose red 724 (Wilson). Outer petals: Upper side of petals—same as center. Reverse of petals—same as center. Base of petals—very small area near white—as compared to yellow base on varieties Tonight, Plant Patent Application Ser. No. 310,030 and Forever Yours, U.S. Plant Pat. No. 2443. General tonality from a distance—near Currant Red 821 (Wilson). Variegations: Occasionally a green streak on outside of outer petal and 3 to 4 white streaks on inside of outer petals.
- *Discoloration.*—On fourth day center of flower lightens to a color between Currant Red 821/3 and Rose Red 724 (Wilson).
- *Fragrance.*—None.

Petals:
- *Texture.*—Thick.
- *Surface.*—Inside—satiny. Reverse—shiny.
- *Shape.*—Round.
- *Form.*—Tips slightly recurved.
- *Arrangement.*—Imbricated.
- *Petaloids in center.*—Few.
- *Persistence.*—Drop off cleanly.
- *Lastingness.*—On the plant—very long. As cut flower—very long.

Reproductive parts:
- *Anthers.*—Medium. Color—yellow. Arrangement—regular around styles.
- *Filaments (threads).*—Short. Color—yellow.
- *Pollen.*—Lemon yellow.
- *Styles.*—Loosely separated, uneven lengths. Color—Crimson. Thin.
- *Stigmas.*—Color—white.
- *Ovaries.*—All enclosed in calyx.

Fruit: Not observed.

PLANT

Form: Bush.

Growth: Very vigorous, upright, branching.

Foliage:
- *Size.*—Medium.
- *Quantity.*—Normal.
- *Color.*—New foliage: near 7.5 R 2/4 (Munsell). Old foliage: mostly when well grown 8.0 G 3/4 (Munsell).

Leaflets: Number of leaflets on normal mid-stem leaves, 5 or 7.
- *Shape.*—Oval pointed.
- *Texture.*—Upper side—leathery . Under side—smooth. Ribs and veins—ordinary.
- *Edge.*—Serrated, undulated.
- *Serration.*—Single, small.

*Petiole.*—Rachis—Color—reddish. Underside—few prickles.

*Stipules.*—Long.

*Disease resistance.*—Moderately resistant to mildew under normal growing conditions at Irvine, Calif., as compared to other cultivars at same location.

Wood:

*New wood.*—Color—light green.

*Bark.*—Smooth.

*Old wood.*—Color—green.

*Bark.*—Smooth.

Prickles:

*Quantity.*—On main stalks from base—ordinary. On laterals from stalk—ordinary.

*Form.*—Broad base, long, straight.

*Color when young.*—Very light brown—sometimes yellowish green.

*Position.*—Irregular.

Small prickles:

*Quantity.*—On main stalks—none. On laterals—none.

I claim:

1. A new and distinct cultivar of rose plant of the hybrid tea class, substantially as herein shown and described, characterized particularly as to novelty by the unique combination of its vigorous, upright habit of growth, suitability as a greenhouse cut flower, its dark green, mildew resistant foliage, its lack of fragrance, its bud and flower color near Wilson's Current Red.

No references cited.

ROBERT E. BAGWILL, Primary Examiner

UNITED STATES PATENT AND TRADEMARK OFFICE

CERTIFICATE OF CORRECTION

PATENT NO. : P.P. 3,727

DATED : June 10, 1975

INVENTOR(S) : William A. Warriner

It is certified that error appears in the above-identified patent and that said Letters Patent are hereby corrected as shown below:

Column 1, line 52, after "U.S. Pl. Pat." insert --2851--

Column 2, line 22, "821/" should be --821/1--

Signed and Sealed this

*nineteenth* Day of *August 1975*

[SEAL]

*Attest:*

RUTH C. MASON
*Attesting Officer*

C. MARSHALL DANN
*Commissioner of Patents and Trademarks*